(12) United States Patent
Gertzman et al.

(10) Patent No.: US 6,548,080 B1
(45) Date of Patent: Apr. 15, 2003

(54) METHOD FOR PARTIALLY DEMINERALIZED CORTICAL BONE CONSTRUCTS

(75) Inventors: Arthur A. Gertzman, Stony Point, NY (US); Moon Hae Sunwoo, Old Tappan, NJ (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 0 days.

(21) Appl. No.: 10/124,424

(22) Filed: Apr. 18, 2002

Related U.S. Application Data (60) Division of application No. 09/739,214, filed on Dec. 19, 2000, now Pat. No. 6,432,436, which is a continuation-in-part of application No. 09/677,891, filed on Oct. 3, 2000, now Pat. No. 6,458,375.

(51) Int. Cl.[7] .............................. A61F 2/28; A61F 2/30; A61F 2/32; A61F 2/38; A61F 2/40
(52) U.S. Cl. ....................... 424/423; 424/422; 424/400; 424/94.1; 424/549; 514/785; 514/801; 514/802
(58) Field of Search .............................. 424/422, 94.1, 424/423, 549; 514/785, 801, 802; 623/16

(56) References Cited

U.S. PATENT DOCUMENTS

| | | | |
|---|---|---|---|
| 5,073,373 A | * | 12/1991 | O'Leary et al. ............ 424/422 |
| 5,290,558 A | | 3/1994 | O'Leary et al. |
| 5,314,476 A | * | 5/1994 | Prewett et al. ............... 623/16 |
| 5,455,041 A | | 10/1995 | Genco et al. |
| 5,507,813 A | | 4/1996 | Dowd et al. |
| 5,556,430 A | * | 9/1996 | Gendler ....................... 623/16 |
| 5,585,116 A | * | 12/1996 | Boniface et al. ............ 424/549 |
| 5,861,167 A | | 1/1999 | Lindskog et al. |
| 5,899,939 A | | 5/1999 | Boyce et al. |
| 5,972,368 A | | 10/1999 | McKay |

FOREIGN PATENT DOCUMENTS

WO    WO 99/39757    8/1999

OTHER PUBLICATIONS

Hallfeldt et al., Sterilization of Partially Demineralized Bone Matrix: The Effects of Different Sterilization Techniques on Osteogenetic Properties; Journal of Surgical Research 59, 1995, pp. 614–620, vol. 59.*

Hallfeldt et al., Sterilization of Partially Demineralized Bone Matrix: The Effects of Different Sterilization Techniques on Osteogenetic Properties; Journal of Surgical Research 59, 1995, pp. 614–620, vol. 59.

* cited by examiner

*Primary Examiner*—Thurman K. Page
(74) *Attorney, Agent, or Firm*—John S. Hale; Gipple & Hale (57) ABSTRACT

The invention is directed toward a sterile bone structure for application to a bone defect site to promote new bone growth at the site comprising a partially demineralized cortical bone structure, said bone structure comprising a cross sectional surface are ranging from 85% to 95% of the original bone surface area before demineralization with the remaining partially demineralized cortical bone structure having an outer demineralized layer ranging in thickness from about 0.05 mm to about 0.14 mm and a mineralized core.

19 Claims, 7 Drawing Sheets

METHOD FOR PARTIALLY DEMINERALIZED CORTICAL BONE CONSTRUCTS

RELATED APPLICATION

The present invention is divisional application of U.S. patent application Ser. No. 09/739,241 now U.S. Pat. No. 6,432,436, filed Dec. 19, 2000 which is a continuation-in-part of U.S. patent application Ser. No. 09/677,891 now U.S. Pat. No. 6,458,375, filed Oct. 3, 2000.

FIELD OF INVENTION

The present invention is generally directed toward a surgical bone product and more specifically is a shaped partially demnineralized allograft bone device or construct with a mineralized central section.

BACKGROUND OF THE INVENTION

The use of substitute bone tissue dates back around 1800. Since that time research efforts have been undertaken toward the use of materials which are close to bone in composition to facilitate integration of bone grafts. Development have taken place in the use of grafts of a mineral nature such as corals, hydroxyapatites, ceramics or synthetic materials such as biodegradable polymer materials. Surgical implants should be designed to be biocompatible in order to successfully perform their intended function. Biocompatibility may be defined as the characteristic of an implant acting in such a way as to allow its therapeutic function to be manifested without secondary adverse affects such as toxicity, foreign body reaction or cellular disruption.

Human allograft tissue is widely used in orthopaedic, neuro-, maxilofacial, podiatric and dental surgery. The tissue is valuable because it is strong, biointegrates in time with the recipient patient's tissue and can be shaped either by the surgeon to fit the specific surgical defect or shaped commercially in a manufacturing environment. Contrasted to most synthetic absorbable or nonabsorbable polymers or metals, allograft tissue is bioinert and integrates with the surrounding tissues. Allograft bone occurs in two basic forms; cancerous and cortical. Cortical bone is a highly dense structure comprised of triple helix strands of collagen fiber, reinforced with hydroxyapatite. The cortical bone is a compound structure and is the load bearing component of long bones in the human body. The hydroxyapatite component is responsible for the high compressive strength of the bone while the collagen fiber component contributes in part to torsional and tensile strength.

Many devices of varying shapes and forms can be fabricated from allograft cortical tissue by machining and surgical implants such as pins, rods, screws, anchors, plates, intervertebral spacers and the like have been made and used successfully in human surgery. These engineered shapes are used by the surgeon in surgery to restore defects in bone to the bone's original anatomical shape. This treatment is well known in the art and is commercially available as demineralized bone.

Allograft bone is a logical substitute for autologous bone. It is readily available and precludes the surgical complications and patient morbidity associated with obtaining autologous bone as noted above. Allograft bone is essentially a collagen fiber reinforced hydroxyapatite matrix containing active bone morphogenic proteins (BMP) and can be provided in a sterile form The demineralized form of allograft bone is naturally both osteoinductive and osteoconductive. The demineralized allograft bone tissue is fully incorporated in the patient's tissue by a well established biological mechanism. It has been used for many years in bone surgery to fill the osseous defects previously discussed.

Demineralized allograft bone is usually available in a lyophilized or freeze dried and sterile form to provide for extended shelf life. The bone in this form is usually very coarse and dry and is difficult to manipulate by the surgeon. One solution to use such freeze dried bone has been provided in the form of a commercially available product, GRAFTON®, a registered trademark of Osteotech Inc., which is a simple mixture of glycerol and lyophilized, demineralized bone powder of a particle size in the range of 0.1 cm to 1.2 cm as is disclosed in U.S. Pat. No. 5,073,373 issued Dec. 17, 1991 forming a gel. Similarly U.S. Pat. No. 5,290,558 issued Mar. 1, 1994, discloses a flowable demineralized bone powder composition using a osteogenic bone powder with large particle size ranging from about 0.1 to about 1.2 cm mixed with a low molecular weight polyhydroxy carrier possessing from 2 to about 18 carbons comprising a number of classes of different compounds such as monosaccharides, disaccharides, water dispersible oligosaccharides and polysaccharides.

A recent version of GRAFTON® product uses relatively large demineralized particles in the carrier to create a heterogenous mixture which provides body or substance to the composition. This material is useful in filling larger defects where some degree of displacement resistance is needed by the filler.

The advantages of using the bone particle sizes as disclosed in the U.S. Pat. Nos. 5,073,373 and 5,290,558 patents previously discussed were compromised by using bone lamellae in the shape of threads or filaments having a median length to median thickness ratio of about 10:1 and higher while still retaining the low molecular weight glycerol carrier. This later prior art is disclosed in U.S. Pat. No. 5,314,476 issued May 24, 1994 and U.S. Pat. No. 5,507,813 issued Apr. 16, 1996 and the tissue forms described in these patents are known commercially as the GRAFTON® Putty and Flex, respective The combination of natural cortical bone with very desirable mechanical strength and the addition of synthetic (recombinant) BMPs provides a superior form of tissue for surgical use retaining all of the mechanical properties of the cortical component and the accelerated healing offered by the BMP's.

U.S. Pat. No. 5,972,368 issued on Oct. 26, 1999 discloses the use of cortical contructs (e.g. a cortical dowel for spinal fusion) which are cleaned to remove all of the cellular material, fat, free collagen and non-collagenous protein leaving structural or bound collagen which is associated with bone mineral to form the trabecular struts of bone. It is stated that the natural crystalline structure of bone is maintained without the risk of disease transmission or significant imnmunogenicity. Thus the shaped bone is processed to remove associated non-collagenous bone proteins while maintaining native bound collagen materials and naturally associated bone minerals. Recombinant BMP-2 is then dripped onto the dowel surface. It could also be added to the cortical bone by soaking in the BMP-2 solution. As noted, this reference teaches the removal of all non-collagenous bone proteins which necessarily include all the naturally occurring BMP 's and relies upon the addition of recombinant BMP-2 in a specific and empirically determined concentration. The naturally occurring BMP's are present in a concentration unique for each specific BMP protein and has been optimized by nature. The '368 patent teaches complete removal of the natural BMP's by demineralization and relies solely on the added rhBNP's. The surface of a machined cortical bone surface is characterized by a wide variety of openings resulting from exposure by the machining process of the Haversian canals present throughout cortical bone. These canals serve to transport fluids throughout the bone to facilitate the biochemical processes occurring within the bone. They occur at variable angles and depths within the bone. Hence, when the machining occurs, the opening will be varied and unpredictable resulting in a highly variable and uncontrolled amount of BMP entering the surface of the bone.

In WO99/39,757 published Aug. 12, 1999, an osteoimplant is disclosed which uses partially demineralized bone elements and adjacent surface-exposed collagen to form chemical linkages to bond the elements into a solid aggregate. It is noted in the Description of the Preferred Embodiments, that "when prepared from bone derived elements that are "only superficially dernineralized" that the osteoimplant will possess a fairly high compression strength approaching that of natural bone. FIG. 2 illustrates bone-derived stacked sheets having a fully or partially demineralized outer surface 21 with surface exposed collagen and a nondemineralized or partially demineralized core 22. As noted in Example 1, the bone sheets approximately 1.5 mm thick were placed in a 0.6N HCl solution for 1.5 hours with constant stirring, washed in water for 5 minutes and soaked for 1.5 hours in phosphate buffered saline. In Example 3 the bone-derived sheets from cortical bone were treated for 10 minutes in 0.6N HCl to expose surface collagen. Bone cubes derived from human cancerous bone were treated to expose surface collagen at the outer borders of the cube. In Example 4, human cortical bone-derived sheets approximately 1 mm thick were surface demineralized for 15 minutes in 0.6N HCl and in Example 5, human cortical bone derived sheets approximately 2 mm thick were surface demineralized for 1 hour in 06N HCl.

U.S. Pat. No. 5,899,939, issued May, 1999, to the same inventor as the foreign patent noted in the paragraph above, discloses a bone derived implant made up of one or more layers of fully mineralized or partially demineralized cortical bone, and optionally one or more layers of some other material. The layers of the implant are assembled into a unitary structure to provide an implant.

In U.S. Pat. No. 5,861,167, issued Jan. 19, 1999, a tooth root is shown to have selective parts of the surface removed by acid to improve subsequent attachment of the tooth in conjunction with periodontal surgery. Similarly U.S. Pat. No. 5,455,041 utilized treatment by demineralizing the tooth root surface with citric acid applied for one minute to effect reattachment of collagen fibers to the root surface and adding growth factors onto the surface of the demineralized root Partial demineralization of bone is also disclosed in the *Journal of Surgical Research* Vol. 59, pages 614–620 (1995) in the article Sterilization of Partially Demineralized Bone Matrix: The Effects of Different Sterilization Techniques on Osteogenetic Properties where particles of bone of 500 microns were treated for 24 hours at 4 degrees C with 0.6 N HC1 with the extent of decalcification determined to be 20% and placed in the bone site. New bone formation was noted after the passage of six weeks.

In French Patent Applications Numbers 2,582,517 and 2,582,518 treatment of fragments of bones taken from animals, primarily cattle were partially demineralized and tanned with glutaraldehyde. The bone elements to be implanted are cut to the desired shape from an ox bone which has been subjected to a treatment comprising a degreasing step with an organic solvent such as ethanol, a demineralization step with a calcium extraction agent such as hydrochloric acid and tanning with glutaraldehyde and subsequent washings. Similar demineralization of bone is shown in U.S. Pat. No. 5,585,116 issued Dec. 17, 1996. This patent also notes that it is known that partial demineralization facilitates integration of a bone graft. This is accordingly followed by different complementary steps which are intended either to deproteinize the bone completely or to act on the nature of the proteins which then remain linked within the bone matrix or else to increase this proportion of proteins.

It is desirable to make the surface of the bone more conductive to receiving BMP's and other additives without losing the desirable high mechanical strength properties of the cortical bone. It is also desirable to leave most of the naturally occurring protein intact in the bone in such a way as to expose just enough of the bone surface to free the natural BMP's present on the surface. Since demineralization also reduces the cross sectional area of the bone construct, the bone construct must retain its shape and structural integrity.

Accordingly, the prior art only partially addresses the problems inherent in correcting surgical defects.

SUMMARY OF THE INVENTION

The present invention is directed toward the treatment of the surface of cortical bone constructs to modify the surface by removing a layer of the inorganic mineral hydroxyapatite material leaving the mechanical properties of the bone constructs substantially unchanged while providing a surface that allows the addition of BMP's and other desirable additives to be introduced to the surface and thereby enhance the healing rate of the cortical bone in surgical procedures.

The subject formulation is a demineralized bone structure for application to a bone defect site to promote new bone growth at the site comprising a partially demineralized cortical bone structure, said bone structure comprising a cross sectional surface are ranging from 85% to 95% of the original bone surface area before demineralization with the remaining partially demineralized cortical bone structure comprising an outer demineralized layer ranging in thickness from about 0.05% to about 0.14%. The structure is designed to present the bone matrix and a demineralized surface layer for reception of bone morphogenetic proteins (BMP) and other desired additives. The macrostructure of the highly porous demineralized surface layer serves both as an osteoconductive matrix and to signal the patient's tissue and cells to initiate the growth of new bone (osteoinduction).

It can be seen that the prior art has attempted to replicate to some degree the present invention by flash demineralization of the surface or fill dernineraliztion of the structure.

It is thus an object of the invention to provide a shaped bone implant construct having a partially demineralized cortical bone layer with an interior mineralized bone section to provide compression strength to the implant bone construct.

It is an object of the invention to utilize a partially demineralized shaped bone implant structure to approximate the mechanical strength characteristics of natural bone to provide overall strength and initial durability to the structure.

It is yet another object of the invention to provide a partially demineralized shaped bone implant structure to provide a strong implant structure of a predetermined shape and size for implantation.

It is also an object of the invention to provide a bone derived structure which can effective hold medical and biological composition which promote new bone growth and accelerate healing.

It is an additional object of the invention to use a BMP additive in the demineralized layer of the bone structure.

It is an still additional object of the invention to use a soluble silver additive in the demineralized layer of the bone structure.

It is also an object off the invention to create a bone structure which can be easily handled by the physician.

These and other objects, advantages, and novel features of the present invention will become apparent when considered with the teachings contained in the detailed disclosure which along with the accompanying drawings constitute a part of this specification and illustrate embodiments of the invention which together with the description serve to explain the principles of the invention.

DETAILED DESCRIPTION OF THE INVENTION

The present invention is directed towards a treated partially demineralized cortical bone construct which can be placed in a bone defect area to heal bone defects. The term cortical bone construct means any shaped bone device such as rods, pins, dowels, screws, plates, wedges, fusion rings, intervertaebral spacers and composite assemblies. The aforementioned listing is exemplary only and is not to construed as restrictive.

The preferred embodiment and the best mode as shown in FIGS. 1 and 7–11 and shows a cylindrical cortical bone construct 10 with its surface 12 modified by acid treatment to remove a layer of the inorganic, mineral, hydroxyapatite bone material in such a way as to leave the mechanical properties substantially unchanged. While the bone material is referred to as hydroxyapatite in this application, in actuality the chemistry and structure of natural bone mineral is different as natural bone mineral contains carbonate ions, magnesium, sodium, hydrogen phosphate ions and trace elements and a different crystalline structure than hydroxyapatite.

The unique features of bone that makes it desirable as a surgical material are, its ability to slowly resorb and be integrated into the space it occupies while allowing the bodies own healing mechanism to restore the repairing bone to its natural shape and function by a mechanism known in the art as creeping substitution. The second feature is the high mechanical strength arising from the collagen fiber reinforced hydroxyapatite compound structure. The creeping substitution mechanism, takes considerable time and some forms of cortical bone in their natural, unmodified biological state have been found to persist for over one year before completely remodeling. Thus a means of accelerating the rate of biointegration of cortical bone would improve the rate of healing and benefit the recipient patient.

It is well known that bone contains osteoinductive elements known as bone morphogenetic proteins (BMP). These BMP's are present within the compound structure of cortical bone and are present at a very low concentrations, e.g. 0.003%. Based upon the work of Marshall Urist as shown in U.S. Pat. No. 4,294,753, issued Oct. 13, 1981 the proper demineraliation of cortical bone will expose the BMP and present these osteoinductive factors to the surface of the demineralized material rendering it significantly more osteoinductive. The removal of the bone mineral leaves exposed portions of collagen fibers allowing the addition of BMP's and other desirable additives to be introduced to the demineralized outer treated surface of the bone structure and thereby enhances the healing rate of the cortical bone in surgical procedures. The treatment process also exposes the naturally occurring BMP's at the surface and renders the surface with biological properties similar to full demineralized bone (DBM). The inner mass 14 of the bone mineral of the shaped construct would be left intact to contain the naturally occurring BMP's and trace elements as noted above. Such a product would be beneficial in spinal fusion, fracture fixation and simlar orthopaedic and neurological procedures where rapid healing without loss of strength of implant is required. Partially demineralized rods 16 as shown in FIG. 1 and FIGS. 7–11 will retain various degrees of stiffness inversely proportional to the degree of demineralization and retention of core mass. The partially demineralized rods have a demineralized outer section 18 of exposed collagen matrix and a cortical bone core 20.

Experiments conducted by the Applicants have discovered that the surface of cortical bone constructs can be modified by acid treatment to remove a layer of the inorganic, mineral, hydroxyapatite material in such a way as to leave the mechanical properties substantially unchanged or to provide a construct having suitable compression and bending strength. This then allows the addition of BMP's and other desirable additives to be introduced to the surface and thereby enhance the healing rate of the cortical bone in surgical procedures. The process also exposes the naturally occurring BMP's near the surface and renders the surface with biological properties similar to fully demineralized bone (DMB). The inner mass of the bone construct would be left intact to contain the naturally occurring BMP's.

It was found that when allograft cortical pins of 2.0 mm diameter were treated as noted below in Example 1; and the pins were soaked for 15 to 30 minutes in a 0.6N solution of HCl that there was minimal loss of bending strength of the rod even when the diameter of the rod was reduced from 3 to 5% and the outer layer was demineratized. The demineralized layer ranged from about 0.05 to about 0.08 mm reducing the mineralized portion diameter from 0.10 mm to 0.16 mm after 15 to 30 minutes of soaking in the 0.6N HCl acid bath.

EXAMPLE 1

Allograft cortical bone pins were prepared by machining femoral or tibial cortical bone. Pins were prepared with diameter of approximately 2.0 mm and a length of 4 cm. The bulk bone segments from which the pins were cut were chemically cleaned before machining by soaking:

1) 30 minutes in an aqueous antibiotic solution of Gentamycin. This reduces and eliminates any bioburden introduced by handling the bone.

2) 30 minutes in an aqueous detergent at 95° F. using ultrasonic energy to enhance penetration. This loosens and removes the lipid elements present in and on the bone.

3) 60 minutes in a 70/30%v/v ethanol/water solution. This further removes any lipid elements remaining after the detergent wash in step 2, above.

4) The final cut pins were given a final soak in a fresh solution of the ethanol/water cleaning solution.

5) The pins were cut in half and then immersed in a 0.6 N solution of Hydrochloric Acid (HCl). Half of each pin was immersed for varying times and the other half was retained as an untreated control.

6) The acid treatment was done at room temperature, 23° C.

7) Acid immersion was done for 30, 60, 90, 120 and 180 minutes. The pins were immersed in the acid solution and agitated with gentle mechanical stirring.

8) After the appropriate elapsed time the pins were removed, washed with sterile, pure (USP Sterile) water until the wash discard was at neutral pH.

9) The pins were then lyophilized and packaged in a moisture permeable container.

For purpose of this example, the above treatments were done in a laboratory setting. In a commercial process, the procedures would be done in a sterile, clean room facility.

The acid treatment can be controlled to remove a small layer of the bone mineral layer leaving a highly porous and compressible surface layer while inducing no change to the inner mass of the construct. By controlling the acid concentration, temperature and time of exposure, a layer up to 0.06 mm can be removed and a layer 0.08 mm demineralized and have the cortical pin experience substantially no loss of mechanical properties as measured by a three-point bending test. This is an unexpected result in that mass loss should have a deleterious effect on bending resistance since the bending moment of a cylindrical beam is a function of the third power of the diameter.

| Demineralization Time | Weight Loss, % (n = 3) | |
|---|---|---|
| [0.6N HCl @ 23° C.] | Average | Std Dev |
| 30 minutes | 31.8 | 3.2 |
| 60 | 38.1 | 1.9 |
| 90 | 48.2 | 1.2 |
| 120 | 56.1 | 6.4 |
| 180 | 64.9 | 2.9 |

The thickness of the demineralized layer was also measured. For each treated pin, the thickness of the demineralized layer was measured six times by starting at the top of the bone traveling clockwise approximately 60°. The following data was measured:

| Demineralization Time [0.6N HCl @ 23° C.] | Thickness of Demineralized Layer (mm) Average (n = 6) |
|---|---|
| 30 minutes | 0.08 |
| 60 | 0.11 |
| 90 | 0.14 |
| 120 | 0.17 |
| 180 | 0.25 |

Figure 1:
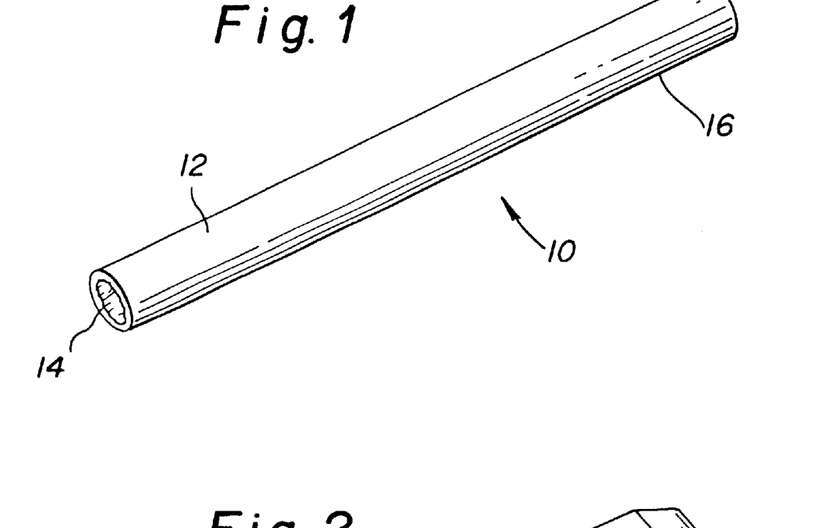
FIG. 1 is a perspective view of a partially demineralized rod or dowel according to the invention.
Figure 2:
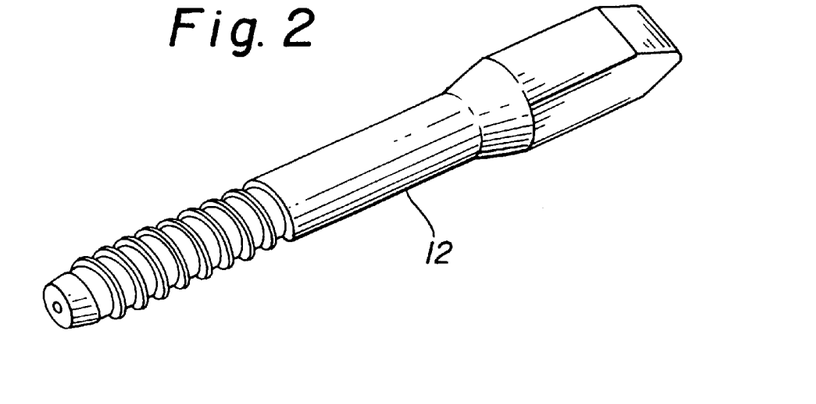
FIG. 2 is a perspective view of a partially demineralized screw according to the invention.
Figure 3:
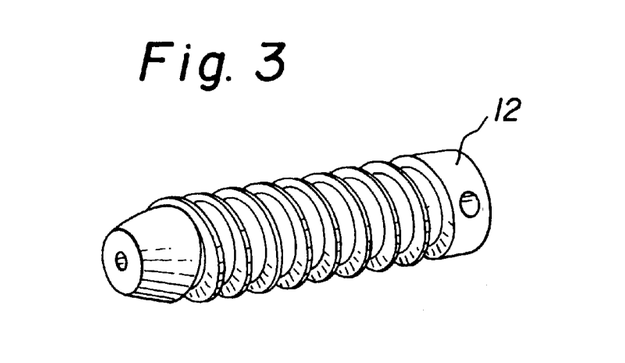
FIG. 3 is a perspective view of a partially demineralized anchor according to the invention.
Figure 4:
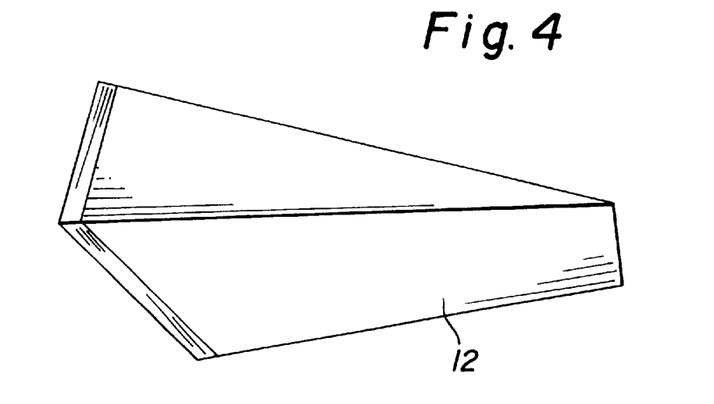
FIG. 4 is a perspective view of a partially demineralized wedge according to the invention.
Figure 5:
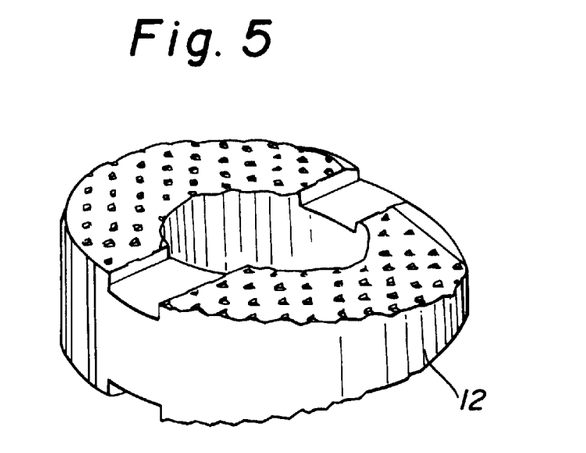
FIG. 5 is a perspective view of a partially demineralized fusion ring according to the invention.
Figure 6:
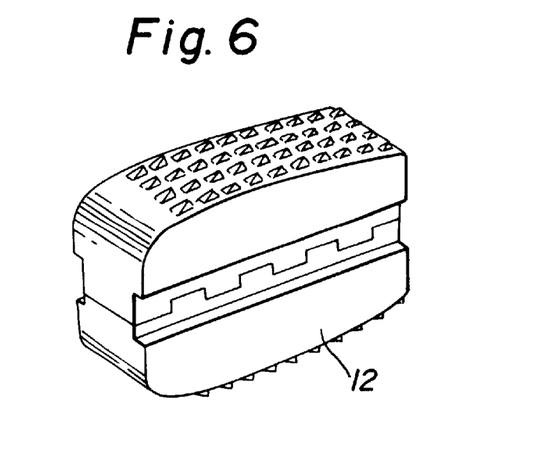
FIG. 6 is a perspective view of a partially demineralized composite structure according to the invention.
Figure 7:
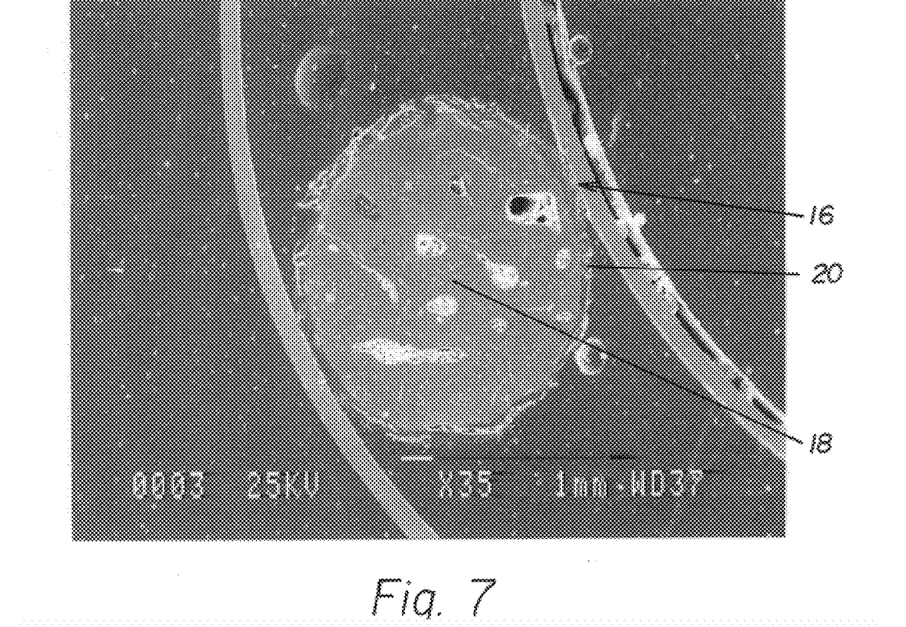
FIG. 7 is a photograph of a 35×enlarged cross sectional view of a partially demineralized rod treated with 0.6N HCl for 30 minutes.
Figure 8:
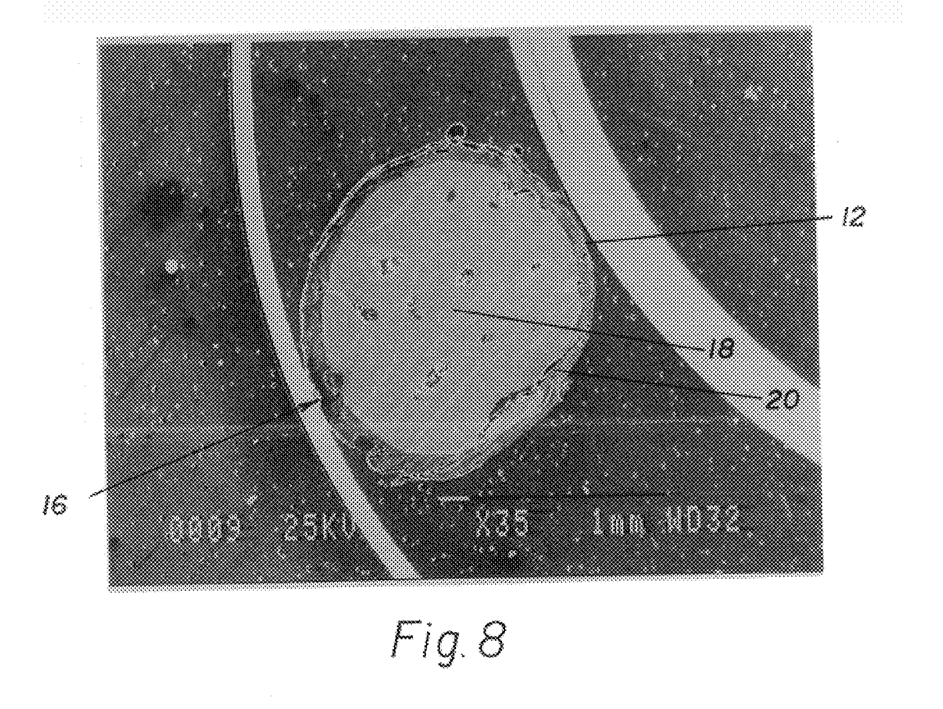
FIG. 8 is a photograph of a 35× enlarged cross sectional view of a partially demineralized rod treated with 0.6N HCl for 60 minutes.
Figure 9:
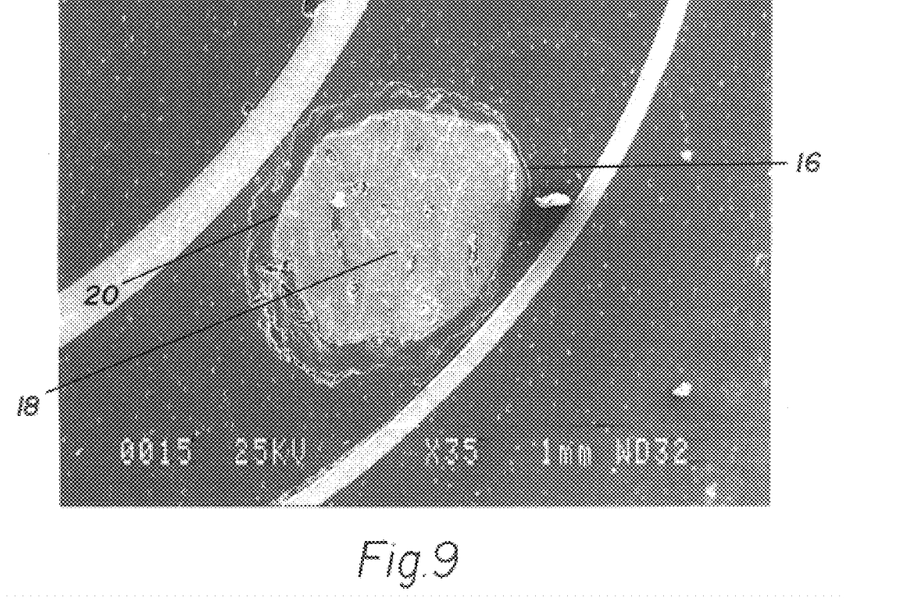
FIG. 9 is a photograph of a 35× enlarged cross sectional view of a partially demineralized rod treated with 0.6N HCl for 90 minutes.
Figure 10:
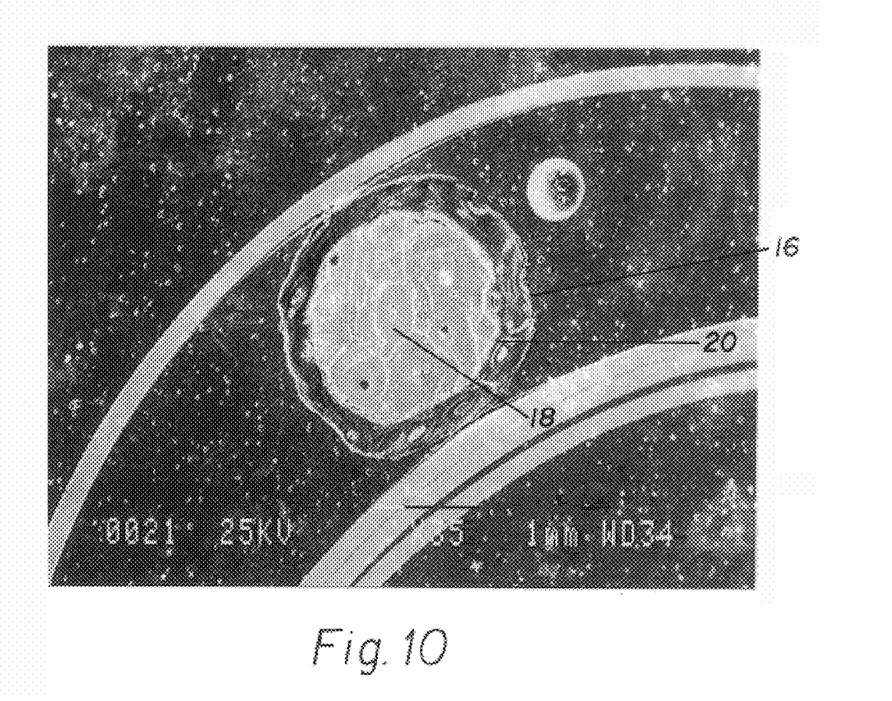
FIG. 10 is a photograph of a 35× enlarged cross sectional view of a partially demineralized rod treated with 0.6N HCl for 120 minutes.
Figure 11:
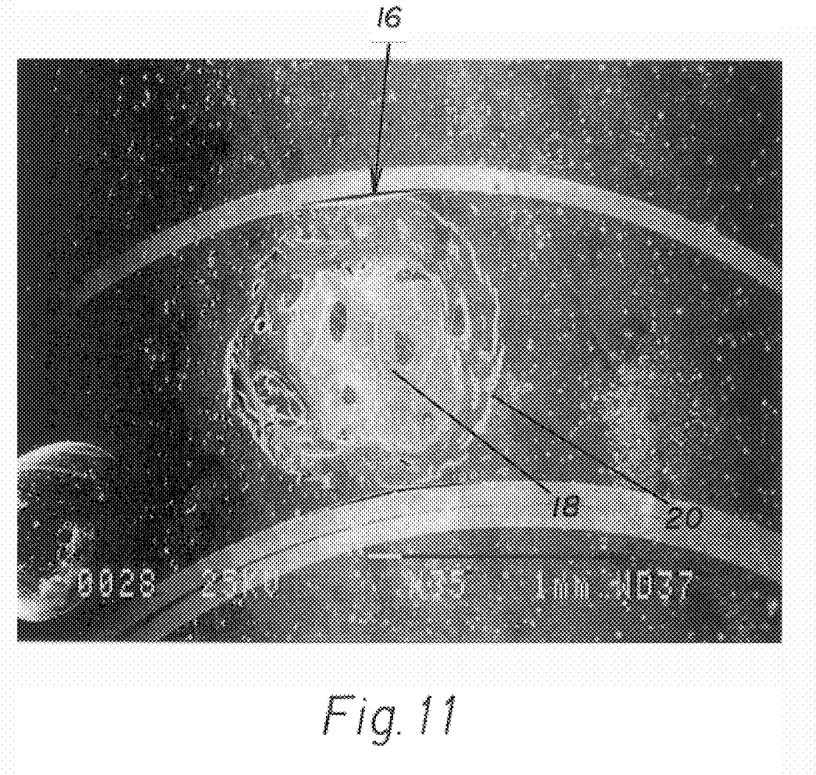
FIG. 11 is a photograph of a 35× enlarged cross sectional view of a partially demineralized rod treated with 0.6N HC1 for 180 minutes.
Figure 12:
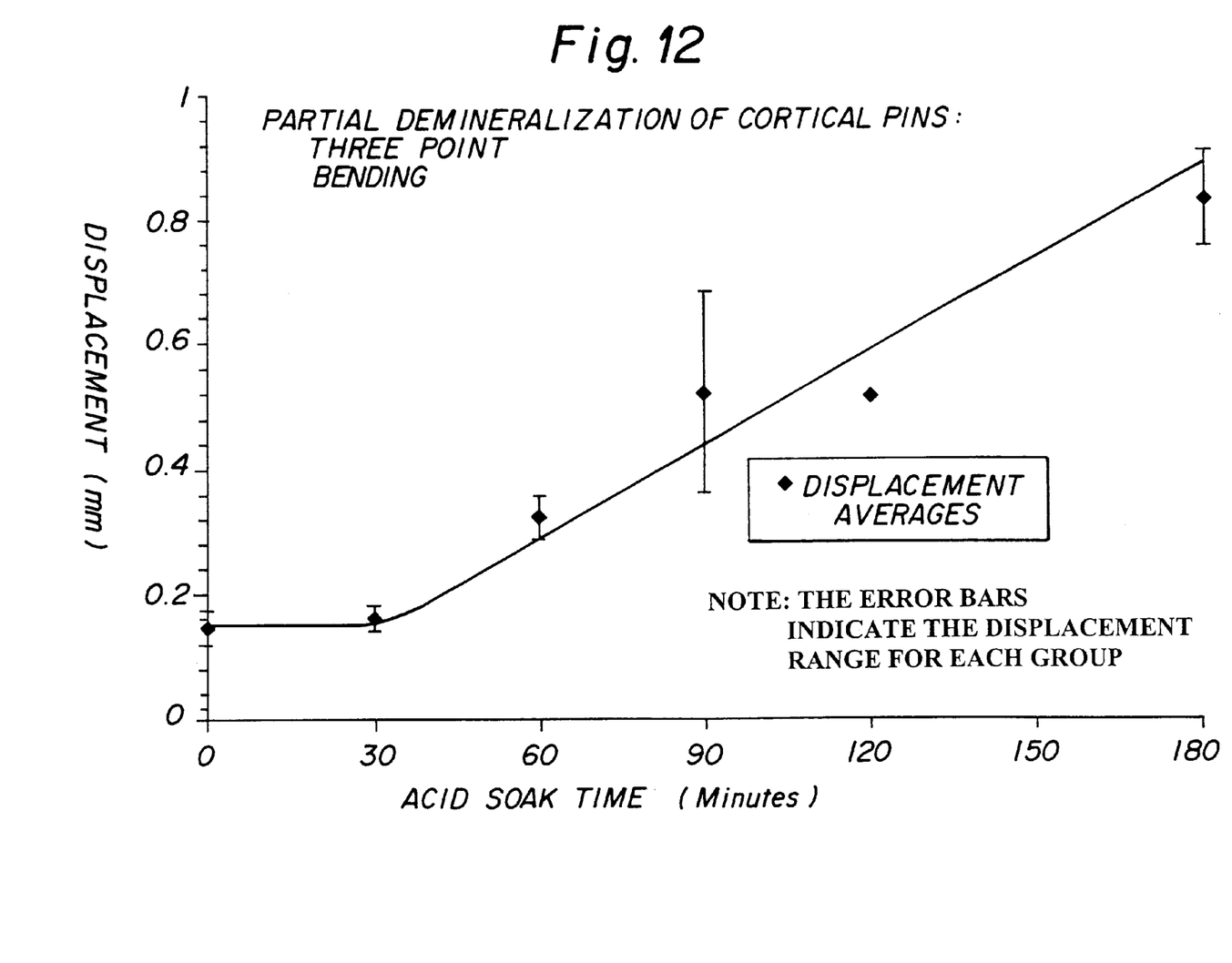
FIG. 12 is a graph showing bending displacement in relation to acid soak time.
Figure 13:
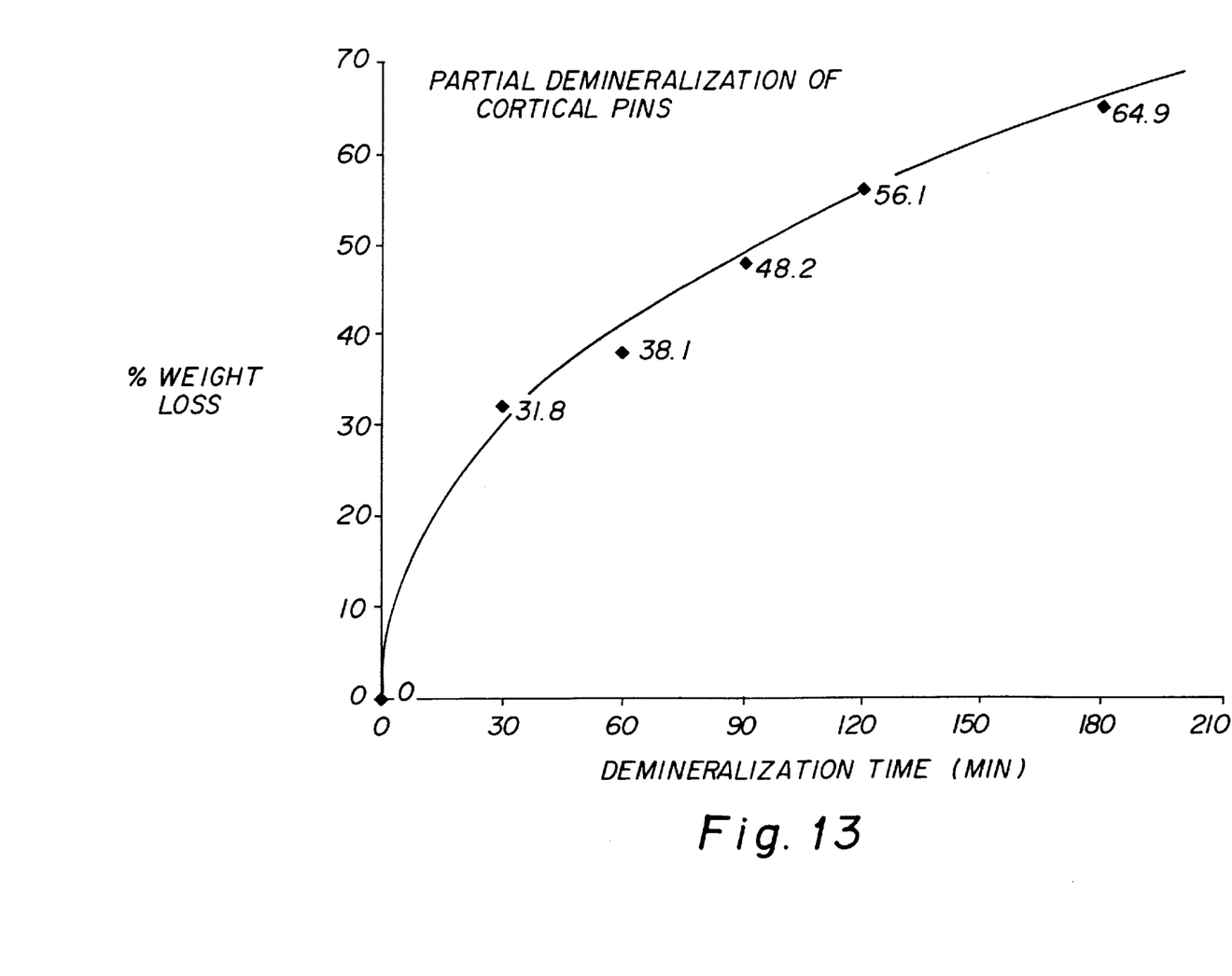
FIG. 13 is a graph showing weight loss during partial demineraliation in relation to acid soak time.

The treated and control pins were subjected to a three-point bending test. Force—displacement calculations were made from the test results as are shown in FIG. 12. Bending displacement appears to be directly proportional to the acid soak time after 30 minutes. It is noteworthy that the bending displacement is equivalent for the 30 minute soak time and the untreated control. Also note that the 30 minute acid treatment did reduce the diameter of the pin 0.12 mm.

Scanning electron micrographs of the treated and control pins were made and can be seen in the FIGS. 7, 8, 9, 10, and 11 reflecting photographs of the same. It can be clearly seen that the Haversian canals can be seen in the cross-section of the acid treated pins and show the removal of the mineral layer at the surface at 35×, revealing the open pores in the demineralized layer exposed by the acid treatment.

This data demonstrates that surface demineralization can be achieved to remove significant amounts of the surface mineral layer without affecting the bulk mechanical strength.

Similar treatments were done for other machined cortical shapes using 0.6N HCl at 23° C. for 10 minutes:

Example 2 Anterior lumbar intervertebral fusion ring (FRA)

Example 3 Posterior lumbar intervertebral fusion block (PLIF)

Example 4 Anterior cervical fusion ring (ACF)

Example 5 Allograft bone screw.

In all these examples, the surface of the machined cortical shape was modified without loss of the key details and dimensions machined into the surface.

The following shows the diameter change, the change in surface morphology, and the size of the dernineralized layers in cylindrical pins that were demineralized in 0.6N HCl in 30, 60, 90, 120, and 180 minutes.

1. Diameter Change

The diameter of each pin was measured in 3 places along the pin. The measurements were recorded on the length of the photograph at 1.5 cm, 6.5 cm, and 11.5 cm on the pin.

Each measurement is recorded in the tables below. The bottom column in each "difference between the treated and untreated pins" is the actual size difference. The pin was magnified ×35 so that the measurements were each divided by 35 to arrive at the actual difference diameter change.

|  | Left Side | Middle | Right Side |
|---|---|---|---|
| Pin 1–30 minute soak |  |  |  |
| Untreated: |  |  |  |
| Pin 1-B1 |  |  |  |
| Measurement | 6.6 cm | 6.4 cm | 6.5 cm |
| Treated: |  |  |  |
| Pin 1-B2 |  |  |  |
| Measurement | 6.0 cm | 6.0 cm | 6.2 cm |
| Difference between the treated and untreated pins |  |  |  |
| Measurement | 0.6 cm | 0.4 cm | 0.3 cm |
| Actual Difference | 0.017 cm | 0.011 cm | 0.009 cm |
| Pin 2–60 minute soak |  |  |  |
| Untreated: |  |  |  |
| Pin 2-A2 |  |  |  |
| Measurement | 6.9 cm | 7.1 cm | 6.5 cm |
| Treated: |  |  |  |
| Pin 2-A2 |  |  |  |
| Measurement | 6.3 cm | 6.3 cm | 6.2 cm |
| Difference between the treated and untreated pins |  |  |  |
| Measurement | 0.6 cm | 0.8 cm | 0.3 cm |
| Actual difference | 0.017 cm | 0.023 cm | 0.009 cm |
| Pin 3–90 minute soak |  |  |  |
| Untreated: |  |  |  |
| Pin 3-C1 |  |  |  |
| Measurement | 7.1 cm | 7.1 cm | 6.9 cm |
| Treated: |  |  |  |
| Pin 3-C2 |  |  |  |
| Measurement | 5.9 cm | 5.6 cm | 5.4 cm |
| Difference between the treated and untreated pins |  |  |  |
| Measurement | 1.2 cm | 1.5 cm | 1.5 cm |
| Actual difference | 0.034 cm | 0.043 cm | 0.043 cm |
| Pin 4–120 minute soak |  |  |  |
| Untreated: |  |  |  |
| Pin 4-A1 |  |  |  |
| Measurement | 6.9 cm | 6.8 cm | 6.6 cm |
| Treated: |  |  |  |
| Pin 4-A2 |  |  |  |
| Measurement | 5.1 cm | 5.2 cm | 4.9 cm |
| Difference between the treated and untreated pins |  |  |  |
| Measurement | 1.8 cm | 1.6 | 1.7 |
| Actual Difference | 0.051 cm | 0.046 cm | 0.049 cm |
| Pin 5–180 minute soak |  |  |  |
| Untreated: |  |  |  |
| Pin 5-A2 |  |  |  |
| Measurement | 6.9 cm | 6.9 cm | 6.7 cm |
| Treated: |  |  |  |
| Pin 5-A2 |  |  |  |
| Measurement | 5.3 cm | 4.6 cm | 5.0 cm |
| Difference between the treated and untreated pins |  |  |  |
| Measurement | 1.6 cm | 2.3 cm | 1.3 cm |
| Actual difference | 0.046 cm | 0.066 cm | 0.037 cm |

Average diameter change for pin 1: 0.012 cm (0.12 mm)
Average diameter change for pin 2: 0.016 cm (0.16 mm)
Average diameter change for pin 3: 0.040 cm (0.40 mm)
Average diameter change for pin 4: 0.049 cm (0.49 mm)
Average diameter change for pin 5: 0.050 cm (0.50 mm)

2. Surface Morphology

The surfaces of the treated pins were compared to the surfaces of the untreated pins.

| Pin Number | Surface Morphology |
|---|---|
| 1-B1 | Particles are held very tightly together. There are small gaps in the bone. It looks somewhat rigid. |
| 1-B2 | Looks looser than 1-B1. Very rough looking. Can see loose particles. There are many holes in the bone. Appears to have more dimension/depth than 1-B1. |
| 2-A1 | Particles are held tightly together. There are many small gaps in the bone. |
| 2-A2 | There are many loose particles. The gaps are wider than 2-A1. |
| 3-C1 | Very dense and rigid-looking. Particles are held tightly together. |
| 3-C2 | Not as dense as 3-C1. There are many small surface holes and a couple of loose particles. |
| 4-A1 | Particles held tightly together. Surface appears very rigid. |
| 4-A2 | Surface smoother than 4-A1. There are many surface holes (some deep enough to see the next layer some just forming). A couple of loose particles. |
| 5-A1 | Very dense and rigid. Small gaps. |
| 5-A2 | Smoother than 5-A1. Many surface holes. Towards the top of the slide, the bone appears bumpy. Gaps are wider than in 5-A1. |

3. Thickness of the Deminineralized Layer

For each treated pin, the thickness of the demineralized layer was measured 6 times and the average per pin was calculated and recorded. Note: The measurements started at the top of the bone and recorded clockwise at approximately 60° intervals. (A magnifying glass with a cm ruler on it was used to measure the demnineralized layer of each pin).

| Pin Number | Measurement Number | | | | | | Average Thickness |
|---|---|---|---|---|---|---|---|
|  | 1 | 2 | 3 | 4 | 5 | 6 |  |
| 1-B2 | 0.09 mm | 0.09 mm | 0.06 mm | 0.11 mm | 0.06 mm | 0.09 mm | 0.08 mm |
| 2-A2 | 0.11 mm | 0.09 mm | 0.09 mm | 0.11 mm | 0.14 mm | 0.11 mm | 0.11 mm |
| 3-C2 | 0.14 mm | 0.06 mm | 0.03 mm | 0.17 mm | 0.29 mm | 0.14 mm | 0.14 mm |
| 4-A2 | 0.17 mm | 0.20 mm | 0.20 mm | 0.17 mm | 0.11 mm | 0.14 mm | 0.17 mm |
| 5-A2 | 0.26 mm | 0.23 mm | 0.20 mm | 0.23 mm | 0.29 mm | 0.29 mm | 0.25 mm |

4. Results

The length of acid soak has an effect on the diameter of the pin. While longer the pin is soaked in 0.6N HCl, the more the diameter changes in size (the diameter gets smaller), a relatively constant diameter was reached after the 120 minutes of soak in the HCC. The average diameter change for the pin soaked for 30 minutes was 0.12 mm; for 60 minutes was 0.16 mm; for 90 minutes was 0.40 mm; and for 120 minutes was 0.49 mm and 180 minutes was 0.50 mm. The cross-section slides show that while the diameter of the pins decreased at an increased amount from soak minutes 60 to 90 lessening from soak minutes 90 to 120, it remaining substantially constant thereafter. The thickness of the demineralized layer increased almost linearly.

The surface morphology was also affected by the acid soaks. All the pins were viewed under a magnification of 100×. The slides of the untreated pins looked rigid, the particles were tightly held into place making the bone to appear dense, and there were small gaps on some sections of the bones. The slides of the treated pins looked completely different than the untreated pins. The treated-pin slides show loose particles, surface holes, widened gaps, and the bones appear to be less dense.

Overall, the length of acid soak time affects the three areas tested in this study:

1. The longer the pin soaks in 0.6N HCl, the actual diameter of the pin decreases up until 120 minutes of acid soak.
2. The longer the pin is in the acid soak, the thickness of the demineralized layer on the bone increases and the core mineralized portion decreases.
3. The acid also has an effect on the surface morphology of the bone. It changes the surface morphology from appearing very dense and rigid (when untreated) to having loose particles and becoming somewhat smoother (when treated).

It is valuable to add soluble silver (e.g. $AgNO_3$) to the surface treated cortical bone structure. This will provide biostatic properties to the construct, i.e., it will inhibit any growth of microorganisms which may be resident on the surface of the cortical tissue or adjacent to it in the surrounding tissue. At sufficiently high concentrations, the silver cation will be fully biocidal. Thus, silver ranging from 10 to 10,000 parts per million may be used.

It is also envisioned to add soluble silver to the surface after treatment to provide biostatic properties inhibiting any growth of microorganisms which may be resident on the surface of the cortical tissue or adjacent to it in the surrounding tissue. Silver which can be added is can be taken from a group consisting of silver nitrate and other soluble or slightly soluble silver compounds such as silver chloride, silver oxide, silver sulphate, silver phosphate, silver acetate, silver perchlorate or silver tartrate.

It is also possible to add one or more rhBMP's to the surface of the treated bone shape by soaking and being able to use a significantly lower concentration of the rare and expensive recombinant human BMP to achieve the same acceleration of biointegration. The addition of other useful treatment agents such as vitamins, hormones, antibiotics, antiviral and other therapeutic agents could also be added to the surface modified layer. BMP directs the differentiation of pluripotential mesenchymal cells into osteoprogenitor cells which form osteoblasts. The ability of freeze dried demineralized cortical bone to facilitate this bone induction principle using BMP present in the bone is well known in the art. However, the amount of BMP varies in the bone depending on the age of the bone donor and the bone processing. Sterilization is an additional problem in processing human bone for medical use as boiling, autoclaving or irradiation over 2.0 Mrads is sufficient to destroy or alter the BMP present in the bone matrix.

The time, temperature and acid concentration can be adjusted to achieve a set of process conditions that will give the same physical result as the above noted examples. Temperature could be lowered to 4° C. and allow the process time to increase to one hour (a four fold increase in process time). Temperatures much above 30° C. will result in too rapid a rate of hydroxyapatite removal and result in a highly variable shape. Conditions could be adjusted to use acid concentrations from about 0.1N to about 2.0N HCl. Lower concentrations will result in a very slow rate of mineral layer removal, not conducive to a commercial process. Higher concentrations will result in a too rapid rate of mineral removal and to a highly varied and uncontrolled surface. Other acids could be used; sulfuric, phosphoric or other mineral acids, organic acids such as acetic; cheating agents such as ethylene diamine tetra acetic acid or other weak acids would also be suitable.

Any number of medically useful substances can be incorporated in the invention by adding the substances to the composition at any steps in the mixing process or directly to the final composition. Such substances include collagen and insoluble collagen derivatives, hydroxyapatite and soluble sods and/or liquids dissolved therein. Also included are antiviricides such as those effective against HIV and hepatitis; antimicrobial and/or antibiotics such as erythromycin, bacitracin, neomycin, penicillin, polymyxin B, tetracycline, viomycin, chloromycetin and streptomycin, cefazolin, ampicillin, azactam, tobramycin, clindamycin and gentamycin. It is also envisioned that amino acids, peptides, vitamins, co-factors for protein synthesis; hormones; endocrine tissue or tissue fragments; synthesizers; enzymes such as collagenase, peptidases, oxidases; polymer cell scaffolds with parenchymal cells; angiogenic drugs and polymeric carriers containing such drugs; collagen lattices; biocompatible surface active agents, antigenic agents; cytoskeletal agents; cartilage fragments, living cells such as chondrocytes, bone marrow cells, mesenchymal stem cells, natural extracts, tissue transplants, bioadhesives, transforming growth factor (TGF-beta), insulin-like growthfactor (IGF-1); growth hormones such as somatotropin; bone digesters; antitumor agents; fibronectin; cellular attractants and attachment agents; immuno-suppressants; permeation enhancers, e.g. fatty acid esters such as laureate, myristate and stearate monoesters of polyethylene glycol, enamine derivatives, alpha-keto aldehydes can be added to the composition All products can also be done in an aseptic environment to maintain a sterile final product or sterilized after production. The cortical bone structure is then placed in a moisture permeable inner container which is placed in a moisture barrier outer container.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

What we claim is:

1. A method for partially demineralizing a previously shaped cortical bone structure comprising the steps of:

a) soaking said previously shaped cortical bone structure in an acid solution for a time period at a temperature less than about 30° C. to remove a layer of the cortical bone structure and produce a demineralized layer on the cortical bone structure ranging from about 0.05 mm to about 0.08 mm with the remaining area comprising mineralized bone, the cortical bone structure after partial demineralization being rigid and maintaining substantially its original mechanical strength;

b) agitating the acid solution and immersed cortical bone structure;

c) removing the cortical bone structure from the acid solution and washing the cortical bone structure until the wash discard is at about a neutral pH;

d) packaging the cortical bone structure in a moisture permeable container; and e) lyophiizig the cortical bone structure.

2. A method as claimed in claim 1 wherein said acid solution is hydrochloric acid ranging in acid concentrations from about 0.1N to about 2.0N HCl.

3. A method as claimed in claim 1 wherein said acid solution consists of a group consisting of hydrochloric acid, sulfuric acid, phosphoric acid, mineral acids and organic acids.

4. A method as claimed in claim 1 wherein said acid solution is a cheating agent ethylene diamine tetra acetic acid.

5. A method for partially dernineralizing a previously shaped hone structure comprising the steps of:

a) soaking said previously shaped cortical bone structure having a thickness greater than 1.5 mm in an acid solution for 30 to 90 minutes at ambient temperature to remove a layer of the cortical bone structure ranging from 0.12 mm to 0.40 mm of the surface area and produce bone structure with a mineralized center section and a demineralized layer around said mineralized center section ranging in thickness from about 0.08 mm to about 0.14 mm bone, the cortical bone structure after demineralization being rigid;

b) simultaneously agitating the acid solution and immersed cortical bone structure by stirring same;

c) removing the partially demineralized cortical bone structure from the acid solution and washing the cortical bone structure with sterile pure water until the wash discard is at about a neutral pH;

d) lyophilizing the cortical bone structure; and e) packaging the cortical bone structure in a moisture permeable container.

6. A method as claimed in claim 5 wherein said acid solution is hydrochloric acid ranging in acid concentrations from about 0.1N to about 2.0N HCl.

7. A method as claimed in claim 5 wherein said acid solution consists of a group consisting of hydrochloric acid, sulfuric acid, phosphoric acid, mineral acids and organic acids.

8. A method as claimed in claim 5 wherein said acid solution is a cheating agent ethylene diamine tetra acetic acid.

9. A method as claimed in claim 5 wherein said acid solution has a temperature ranging from between 4° C. and 30° C.

10. A method for partially demineralizing a previously shaped bone structure comprising the steps of:

a) soaking a formed cortical bone structure in an aqueous antibiotic solution;

b) placing the soaked cortical bone structure in an aqueous detergent at about 95 degrees F;

c) applying ultrasonic energy to enhance penetration of said detergent;

d) washing the shaped cortical bone structure for at least 60 minutes in an alcohol/water solution;

e) soaking a formed cortical bone structure in an acid solution for 15 to 30 minutes to remove a layer of the cortical bone structure and produce a demineralized layer ranging from about 0.05 mm to 0.08 mm in thickness bone, the cortical bone structure after demminerazzation being rigid;

f) agitating the acid solution with said immersed cortical bone structure;

g) removing the cortical bone structure from the acid solution and washing the cortical bone structure until the wash discard is at about a neutral pH;

h) lyophilizing the cortical bone structure; and i) packaging the cortical bone structure in a moisture permeable container.

11. A method as claimed in claim 10 wherein said acid solution consists of a group consisting of hydrochloric acid, sulfuric acid, phosphoric acid, mineral acids and organic acids.

12. A method as claimed in claim 10 wherein said acid solution is a cheating agent ethylene diarine tetra acetic acid.

13. A method as claimed in claim 10 wherein said acid solution is hydrochloric acid having a concentration ranging from about 0.1N to about 2.0N HCl and said acid soaking takes place at a temperature ranging from between 4° C. and 30° C.

14. A method as claimed in claim 10 wherein said aqueous antibiotic solution is Gentamysin.

15. A method as claimed in claim 10 wherein after step g), BMP is added to the demineralized layer.

16. A method as claimed in claim 10 wherein after step g), antimicrobial and/or antibiotics selected from the group consisting of erythromycin, bacitracin, neomycin, penicilln, polymyxin B, tetracycline, viomycin, chloromycetin and streptomycin, cefazolin, ampicillin, azactam, tobramycin, clindamycin and gentamycin is added to the demineralized layer.

17. A method for partially demineralizing a previously shaped bone structure comprising the steps of:

a) soaking a formed cortical bone structure in an aqueous antibiotic solution;

b) placing the soaked cortical bone structure in an aqueous detergent at about 95 degrees F;

c) applying ultrasonic energy to enhance penetration of said detergent;

d) washing the shaped cortical bone structure for at least 60 minutes in an alcohol/water solution;

e) soaking a formed cortical bone structure in an acid solution for 15 to 30 minutes to remove a layer of the cortical bone structure and produce a demineralized layer ranging from about 0.05 mm to 0.08 mm in thickness bone, the cortical bone structure after demineralization being rigid;

f) agitating the acid solution with an immersed cortical bone structure;

g) removing the cortical bone structure from the acid solution and washing the cortical bone structure until the wash discard is at about a neutral pH;

h) adding a soluble silver compound to the demineralized layer;

i) lyophilizing the cortical bone structure; and j) packaging the cortical bone structure in a moisture permeable container.

18. A method as claimed in claim 17 wherein said soluble silver compound contains silver in a range of 10 to 10,000 parts per million.

19. A method for partially dernineralizing a previously shaped cortical bone structure comprising the steps of:

a) soaking said previously shaped cortical bone structure in an acid solution for a time period at a temperature less than about 30° C. to remove a layer of the cortical bone structure while maintaining a cross sectional area of the cortical bone structure ranging from about 85% to about 95% and produce a demineralized layer on the cortical bone structure ranging from about 0.05 mm to about 0.08 mm with the remaining area comprising mineralized bone, the cortical bone structure after partial demineralization being rigid and maintaining suitable compression and bending strength;

b) agitating the acid solution and immersed cortical bone structure;

c) removing the cortical bone structure from the acid solution and washing the cortical bone structure until the wash discard is at about a neutral pH;

d) packaging the cortical bone structure in a moisture permeable container; and e) lyophilizing the cortical bone structure.

* * * * *